United States Patent [19]

Hüschelrath et al.

[11] Patent Number: 4,665,752

[45] Date of Patent: May 19, 1987

[54] ELECTRODYNAMIC TRANSDUCER

[75] Inventors: Gerhard Hüschelrath, Laufach; Ewald Kowol, Wehrheim, both of Fed. Rep. of Germany

[73] Assignee: Nukem GmbH, Hanau am Main, Fed. Rep. of Germany

[21] Appl. No.: 749,566

[22] Filed: Jun. 27, 1985

[30] Foreign Application Priority Data

Jul. 10, 1984 [DE] Fed. Rep. of Germany ....... 3425386

[51] Int. Cl.⁴ .......................................... G01N 29/04
[52] U.S. Cl. .................................................. 73/643
[58] Field of Search .......................... 73/643; 336/130

[56] References Cited

U.S. PATENT DOCUMENTS 4,480,477 11/1984 Hüschelrath et al. ............... 73/643

Primary Examiner—Anthony V. Ciarlante
Attorney, Agent, or Firm—Cushman, Darby & Cushman

[57] ABSTRACT

An electrodynamic transducer (10) is disclosed for non-destructive material testing comprising at least one internal pole shoe (16) of an electromagnet with core (12) and magnetic winding (14). The end section (18) of the internal pole shoe (16) is arranged eccentrically in relation to the center axis (29) of the core (12) and is designed to rotate with the core (12) about the center axis (29) thereof.

8 Claims, 2 Drawing Figures

ELECTRODYNAMIC TRANSDUCER

BACKGROUND OF THE INVENTION

The invention relates to an electrodynamic transducer for non-destructive material testing by ultra-sonic means with an electro-magnet having a core surrounded by a magnetic winding in a fixed position in the transducer, and at least one internal pole shoe extending from the core and one corresponding external pole shoe, the internal pole having excitation and receiver coils arranged on the end section thereof facing the electrically conductive workpiece, which is to be tested.

In order to be able to test sheet metal, tank floors and other electrically conductive flat objects, it is desirable to use testing methods in which the necessary number of test heads is small, that is to say, providing the largest possible testing track width. To satisfy these requirements eddy-current transmitters or ultra-sonic test heads with water coupling can be used, whereby the probes are arranged to oscillate, or to rotate on a disc (Material Test 16 (1974) No. 9, September, pages 281-282). However, the disadvantage of eddy-current probes is that only defects close to the surface can be detected. Against this eddy-current probes cannot carry out any dimension measurements. Moreover, eddy-current probes are insensitive to the frequently occurring doubling effects. When using piezo test heads it is necessary to couple via a water path, whereby it is difficult and technically extravagant to achieve a rotating system.

Moreover, with oscillating systems, due to the oscillation frequency (1-2 Hz), it is either impossible or only possible at great expense to achieve a high testing speed by multiplying the number of heads.

If one uses the electrodynamic transducer described above (e.g., as described in DE-OS No. 31 23 935 or EP-A2-No. 0045412), one can determine flaws and thickness without needing to couple via a water path. In these transducers the internal pole shoe is always arranged in rotational symmetry with the center axis of the core of the electromagnet, whereby excitation and receiver coils can be arranged on the free end of the internal pole shoe, or to the side thereof. However, the high weight of such heads gives rise to large centrifugal forces when rotating, or high acceleration when oscillating.

SUMMARY OF THE INVENTION

The object of this invention is to form an electrodynamic transducer of the type described in the opening such that a wide track width can be achieved without necessitating rotation or oscillation of the complete transducer, so that neither high centrifugal forces nor large acceleration forces occur.

According to the invention, the task is achieved in that the end section is offset in relation to the center axis of the core, and is rotatable together with the core about the center axis thereof. In other words, the end section of the internal pole shoe carrying the excitation and receiver coils follows a circular orbit which is concentric with the core axis of the electromagnet. The separation distance, center axis to end section, defines half of the required track width thus making it possible to achieve a broad width track by taking simple structural measures. This involves support by means of ball bearing units between the core and the internal pole shoe projecting from it to allow friction-free motion. The internal core itself can be driven by means of a drive belt.

The external pole shoe corresponding to the internal pole shoe can now either rotate synchronously, or be designed to be stationary relative to the magnetic winding and to extend along the orbit of the end section. Seen in plan elevation, this consequently results in a ring-shaped geometry for the external pole shoe.

In particular, the inventive theory achieves the advantage of avoiding the need for the relatively large mass represented by the magnetic windings, to rotate with the system. This makes speeds of 200-300 r.p.m. possible. Moreover, the necessary clearance space for rotation about the radius of the magnetic winding is smaller in comparision with the conventional rotation of the complete testing head. Smaller scale installation measures are consequently needed. With reference to the piezo test heads used, there is the advantage that, as against the significantly more complex mechanism, above all no coupling medium is required.

In further development of the invention, two internal pole shoes, preferably mutually diameterical, project from the core with their end sections, which—according to the invention—are arranged eccentrically in relation to the centre axis of the core. If only one internal pole shoe is present, it can be provided with a counter-balance element for mass balancing purposes.

In accordance with a further development of the invention, the internal pole shoe and the counter-balance include a cylindrical section projecting from the external face of the core and at an angle offset to its centre axis. Where this concerns the internal pole shoe, the end section is detachable and, at the outer end face of the cylindrical section with the excitation and receiver coils, takes the form of a pole shoe head. This has the advantage that, without altering the actual arrangement of the pole shoes it is easy to change the pole shoe head, i.e., the end section, in the event of damage to the excitation and receiver coil.

In order to largely reduce the risk of damaging them, the excitation and receiver coils have a protective cap projecting towards the workpiece to be tested. This protective cap can be made of metal with a nitrated surface and have radial slots. Alternatively, the protective cap can have a layer of synthetic stone such as sapphire, which is directed towards the workpiece and supported on it.

BRIEF DESCRIPTION OF THE DRAWINGS

The invention is explained in more detail below on the basis of the preferred design example, as shown in accompanying drawings.

The following are shown by.

DETAILED DESCRIPTION OF THE PREFERRED EMBODIMENT

Figure 1:
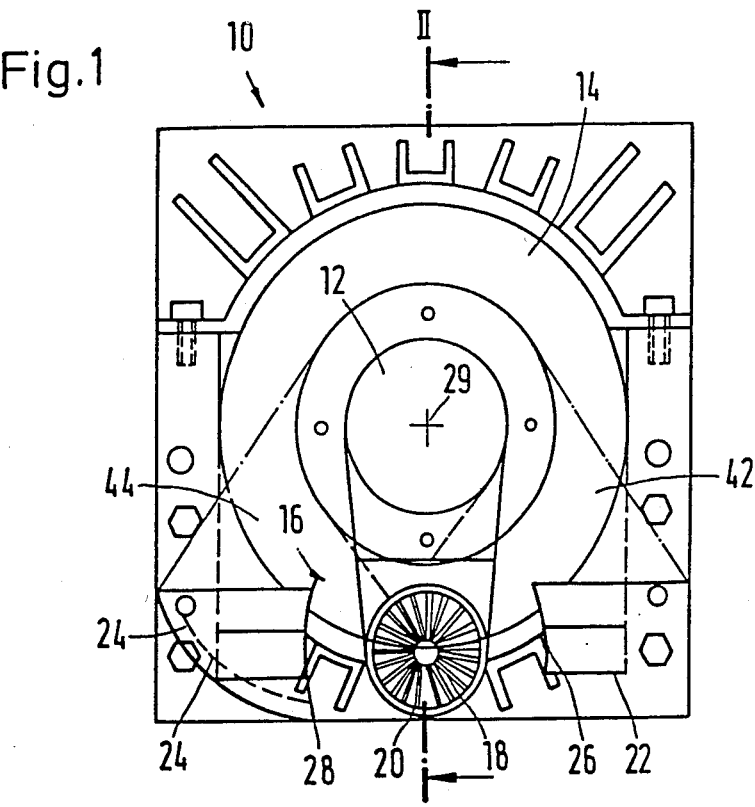
FIG. 1 An electrodynamic transducer in plan elevation.

The two Figures show an electrodynamic transducer head 10, which encompasses an electro-magnet with core 12 and the magnetic winding 14 surrounding the latter. The electro-magnet has an internal pole shoe generally designated by the number 16, as well as a corresponding pair of external pole shoes 22, 24. The internal pole shoe 16 extends from the core 12, and encompasses an end section 18 also designated as a pole shoe head, and on which are arranged the excitation and receiver coils (not shown), which in turn are protected against damage by a cap 20. This measure is necessary, since the transducer head 10 is lowered directly onto the workpiece concerned, which latter can, for example, take the form of a metal sheet, a tank floor or another flat electrically conductive object. The protective cap 20 can be made of metal, preferably with nitrated surface, and have radially running slots, these latter being needed in order to prevent the formation of eddy-currents. As an alternative, the protective cap can also have a layer of synthetic stone such as sapphire, which is lowered directly onto the workpiece.

The face areas 26, 28 of the external pole shoe pair 22, 24 corresponding to the internal pole shoe 16 are concave where they face the rotationally symmetrical pole shoe head 18. That is to say, they exhibit a geometry approximating to that specified in DE-A No. 31 23 935.

Figure 2:
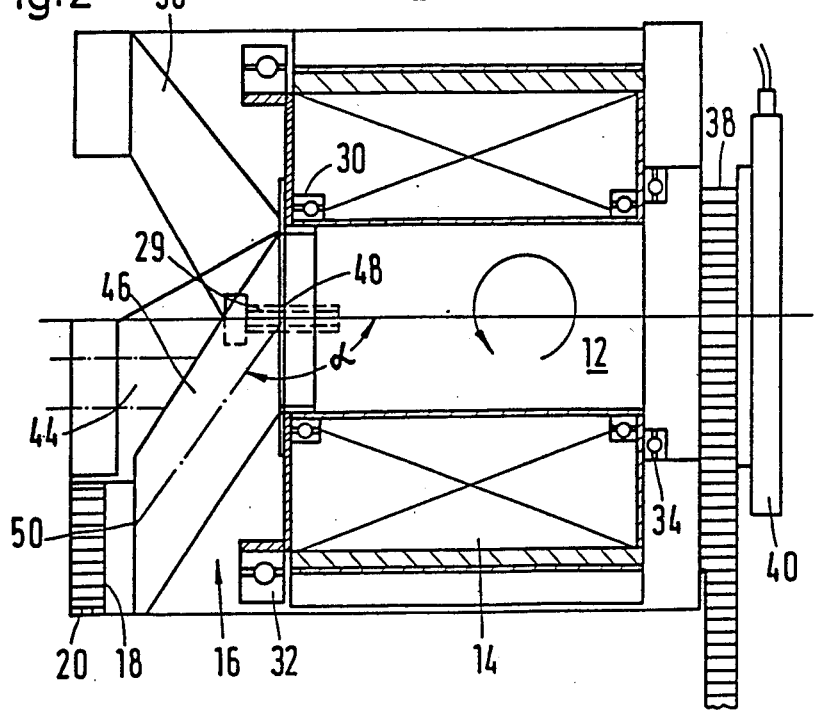
FIG. 2 A cross-sectional representation of the transducer along the line II—II.

As FIGS. 1 and 2 are intended to illustrate, the end section 18 of the internal pole shoe 16 is eccentric in relation to the center axis 29 of the electro-magnet core 12. Moreover, the core 12 with the internal pole shoe 16 and the external pole shoe pair 22, 24, is supported by the ball bearing units 30, 32, 34 in order to carry out a rotational motion without movement of the magnetic winding 14. The resulting advantage is that the magnetic winding 14, as a relatively large mass, does not rotate together with the internal and external pole shoes 16, 22, 24. This consequently also eliminates large centrifugal forces. If the external and the internal pole shoes 22, 24, 16 are now set into rotation, the track width of the invented electrodynamic transducer will be equal to double the distance between the center axis 29 and pole shoe head 18. As a consequence, the required track width can be defined by specifying the distance from the center axis 29, of the core 12, and the pole shoe 18.

The pole shoe 18 is detachably arranged on a cylindrical section 46 of the internal pole shoe 16, and extends from the outer face 48 of core 12, also preferably detachable. The principal axis of the cylindrical section 46 thereby runs at an angle $\alpha$ with $90° < \alpha < 180°$ to the center axis 29. The pole shoe head 18 is then detachably secured to the outer face 50 of the cylindrical section 46.

If the example design foresees the external pole shoes 22, 24 rotating synchronously with the internal pole shoe 16 then, as an alternative, the external pole shoe can take the form of a closed body with a ring-shaped plan elevation, which extends along the orbit of the internal pole shoe 16.

As the cross-sectional view in FIG. 2 shows, a counter-balance 36 is provided for the angled section 46 of the internal pole shoe 16, so as to achieve mass balancing. If required, a further internal pole shoe (2nd probe head) can be fitted in place of the counter-balance; the design of this additional pole shoe must correspond to that of the internal pole shoe 16 with pole shoe head 18 and cover 20 (1st probe head), as initially described. In this case, of course, the additional internal pole shoe must also be allocated a pair of external pole shoes in so far as they are to be rotated together with the internal pole shoe.

The rotation of the internal pole shoe 16 with core 12 and, if necessary, external pole shoes 22 and 24, can be achieved by a flange 38, which is connected on the back of the electromagnet with the core 12, and rotated by a toothed drive belt, for instance. Signal transmission between the excitation and receiver coils is achieved by the schematically represented slip rings 40. Attention is also drawn to the fact that the external pole shoe pair 22, 24 can be supported relative to the core 12 in the face area of the transducer head 10. This can be achieved via connecting elements 42, 44 made of non-ferric material.

We claim:

1. An electrodynamic transducer for non-destructive material testing by ultra-sonic means, comprising:
   an electromagnet having a core
   a magnetic winding surrounding said core and being in a fixed position in the transducer;
   at least one internal pole shoe extending from the core; and
   at least one outer pole shoe corresponding to said at least one inner pole shoe,
   said internal pole having excitation and receiver coils arranged on an end section thereof facing an electrically conductive workpiece to be tested, the end section being arranged off-center relative to a central axis of said core and the end section being rotatable with the core around the central axis thereof relative to the magnetic winding.

2. An electrodynamic transducer according to claim 1, said at least one internal pole shoe being designed to rotate with said at least one external pole shoe synchronously relative to said magnetic winding.

3. An electrodynamic transducer according to claim 1, said at least one external pole shoe extending along the rotational path of said at least one internal pole shoe, and being statically positioned in relation to said magnetic winding.

4. An electrodynamic transducer according to claim 1, comprising two external pole shoes projecting from said core each of said two external pole shoes having excitation and receiver coils on respective end sections arranged eccentrically in relation to the central axis of said core.

5. An electrodynamic transducer according to claim 1, said at least one internal pole shoe having an angled section projecting from said core and being angled in relation to the central axis, and having its free end forming the end section.

6. An electrodynamic transducer according to claim 1, said at least one internal pole shoe being provided with a counter-balancing element for mass balancing purposes.

7. An electrodynamic transducer according to claim 6, said angled section of said at least one internal pole shoe, or said counter-balancing element being arranged diametrically in relation to the central axis of said core.

8. An electrodynamic transducer according to claim 5, said end section being in the form of a pole shoe head and carrying the excitation and receiver coils arranged in detachable form on the outer face of said angled section, which projects from said core and which is angled from the central axis of said core.

* * * * *